US005728557A

United States Patent [19]

Register et al.

[11] Patent Number: 5,728,557

[45] Date of Patent: Mar. 17, 1998

[54] METHOD OF MAKING HERPES SIMPLEX TYPE 1 MUTANTS AND MUTANTS SO PRODUCED

[75] Inventors: R. Bruce Register, Lansdale; Jules A. Shafer, Gwynedd Valley, both of Pa.

[73] Assignee: Merck & Co., Inc., Rahway, N.J.

[21] Appl. No.: 458,067

[22] Filed: Jun. 1, 1995

[51] Int. Cl.[6] .................................................. C12N 15/00

[52] U.S. Cl. .................................. 435/172.3; 435/320.1; 435/364

[58] Field of Search ............................ 435/172.3, 172.1, 435/239, 320.1, 364; 935/32, 57

[56] References Cited

U.S. PATENT DOCUMENTS 5,266,489 11/1993 Rey-Senelonge et al. .......... 435/320.1

FOREIGN PATENT DOCUMENTS

WO 92/03917 3/1992 WIPO .

OTHER PUBLICATIONS

C. Cunningham et al., Virology 197, (1993) 116–124.
I. C. Deckman et al., Journal of Virology 66, (1992) 7362–7367.
C. L. DiIanni et al., Journal of Biological Chemistry 266, (1993) 25449–25454.
L. Matusick-Kumar et al., Journal of Virology 68, (1994) 5384–5394.
M. Gao et al., Journal of Virology 68, (1994) 3702–3712.
C. Addison et al., Virology 138 (1984) 246–259.
F. Liu et al., Proc. Natl. Acad. Sci. USA 89, (1992) 2076–2080.
P. L. Drake et al., The Journal of Biological Chemistry 269 (1994) 18708–18711.
C. L. DiIanni et al., The Journal of Biological Chemistry 268 (1993) 2048–2051.
V. G. Preston et al., Virology 186 (1992) 87–98.
L. Haarr et al., APMIS 102 (1994) 321–346.
W. Batterson et al., Journal of Virology 45 (1983) 397–407.
Desai et al., "The size and symmetry of B capsids of herpes simplex virus type 1 are determined by the gene products of the UL26 open reading frame", J. Virol., 68(9): 5365–5374, Sep. 1994.
Shih et al., "Expression of hepatitis B virus S gene by herpes simplex virus type 1 vectors carrying alpha–and beta–regulated gene chimeras", Proc. Nat. Acad. Sci. USA, 81: 5867–5870, Sep. 1984.
Sanders, et al., "Thymidine kinase muatnts of herpes simplex virus type 1", J. Gen. Virol., 63: 277–295, 1982.
Gaitanaris et al., "Reconstitution of an operon from overlapping fragments: use of lambda SV2 integrative cloning system", Gene 46 : 1–11, 1986.
McGeoch et al., "The complete DNA sequence of the long unique region in the genome of herpes simplex virus type 1", J. Gen. Virol. 69: 1531–1574, 1988.

*Primary Examiner*—James Ketter
*Assistant Examiner*—Irem Yucel
*Attorney, Agent, or Firm*—Joanne M. Giesser; Jack L. Tribble

[57] ABSTRACT

A method for introducing a mutation into a desired site in Herpes Simplex Virus Type 1 uses a set of starting vectors, where each starting vector has a fragment of the substantially complete HSV-1 genome and also DNA which overlaps with a sequential genomic fragment contained in other starting vectors, so that upon co-transfection of a host cell, replication of viral DNA, and recombination, a mutated replicable virus is formed. The starting vector containing a gene which is to be mutated is replaced by a replacement vectors. The replacement vectors contain a copy of the mutated gene and overlapping DNA, and genomic DNA which was present in the starting vector. A host cell is transformed with the replacement vectors and the remaining starting vectors under conditions allowing replication of viral DNA and recombination to form a replicating mutated virus. In preferred embodiments, the protease gene is mutated.

28 Claims, 4 Drawing Sheets

```
ATGGCAGCCGATGCCCCGGGAGACCGGATGGAGGAGCCCCTGCCAGACAGGGCCGTGCCC  60
MetAlaAlaAspAlaProGlyAspArgMetGluGluProLeuProAspArgAlaValPro

ATTTACGTGGCTGGGTTTTTGGCCCTGTATGACAGCGGGGACTCGGGCGAGTTGGCATTG 120
IleTyrValAlaGlyPheLeuAlaLeuTyrAspSerGlyAspSerGlyGluLeuAlaLeu

GATCCGGATACGGTGCGTGCGGCCCTGCCTCCGGATAACCCACTCCCGATTAACGTGGAC 180
AspProAspThrValArgAlaAlaLeuProProAspAsnProLeuProIleAsnValAsp

CACCGCGCTGGCTGCGAGGTGGGGCGGGTGCTGGCCGTGGTCGACGACCCCCGCGGGCCG 240
HisArgAlaGlyCysGluValGlyArgValLeuAlaValValAspAspProArgGlyPro

TTTTTTGTGGGACTGATCGCCTGCGTGCAACTGGAGCGCGTCCTCGAGACGGCCGCCAGC 300
PhePheValGlyLeuIleAlaCysValGlnLeuGluArgValLeuGluThrAlaAlaSer

GCTGCGATTTTCGAGCGCCGCGGCCGCCGCTCTCCCGGGAGGAGCGCCTGTTGTACCTG 360
AlaAlaIlePheGluArgArgGlyProProLeuSerArgGluGluArgLeuLetTyrLeu

ATCACCAACTACCTGCCCTCGGTCTCCCTGGCCACAAAACGCCTGGGGGGCGAGGCGCAC 420
IleThrAsnTyrLeuProSerValSerLeuAlaThrLysArgLeuGlyGlyGluAlaHis

CCCGATCGCACGCTGTTCGCGCACGTCGCGCTGTGCGCGATCGGGCGGCGCCTCGGCACT 480
ProAspArgThrLeuPheAlaHisValAlaLeuCysAlaIleGlyArgArgLeuGlyThr

ATCGTCACCTACGACACCGGTCTCGACGCCGCCATCGCGCCCTTTCGCCACCTGTCGCCG 540
IleValThrTyrAspThrGlyLeuAspAlaAlaIleAlaProPheArgHisLeuSerPro

GCGTCTCGCGAGGGGGCGCGGCGACTGGCCGCCGAGGCCGAGCTCGCGCTGTCCGGACGC 600
AlaSerArgGluGlyAlaArgArgLeuAlaAlaGluAlaGluLeuAlaLeuSerGlyArg
```

FIG. 1A

```
ACCTGGGCGCCCGGCGTGGAGGCGCTGACCCACACGCTGCTTTCCACCGCCGTTAACAAC 660
ThrTrpAlaProGlyValGluAlaLeuThrHisThrLeuLeuSerThrAlaVlaAsnAsn

ATGATGCTGCGGGACCGCTGGAGCCTGGTGGCCGAGCGGCGGCAGGCCGGGATCGCC 720
MetMetLeuArgAspArgTrpSerLeuValAlaGluArgArgArgGlnAlaGlyIleAla

GGACACACCTACCTCCAGGCGAGCGAAAAATTCAAAATGTGGGGGCGGAGCCTGTTTCC 780
GlyHisThrTyrLeuGlnAlaSerGluLysPheLysMetTrpGlyAlaGluProValSer

GCGCCGGCGCGCGGGTATAAGAACGGGGCCCCGGAGTCCACGGACATACCGCCCGGCTCG 840
AlaProAlaArgGlyTyrLysAsnGlyAlaProGluSerThrAspIleProProGlySer

ATCGCTGCCGCGCCGCAGGGTGACCGGTGCCCAATCGTCCGTCAGCGCGGGGTCGCCTCG 900
IleAlaAlaAlaProGlnGlyAspArgCysProIleValArgGlnArgGlyValAlaSer

CCCCCGGTACTGCCCCCCATGAACCCCGTTCCGACATCGGGCACCCCGGCCCCCGCGCCG 960
ProProValLeuProProMetAsnProValProThrSerGlyThrProAlaProAlaPro

CCCGGCGACGGGAGCTACCTGTGGATCCCGGCCTCCCATTACAACCAGCTCGTCGCCGGC 1020
ProGlyAspGlySerTyrLeuTrpIleProAlaSerHisTyrAsnGlnLeuValAlaGly

CACGCCGCGCCCCAACCCCAGCCGCATTCC 1050
HisAlaAlaProGlnProGlnProHisSer
```

FIG. 1B

SEQUENCE LISTING ( 1 ) GENERAL INFORMATION:

( i i i ) NUMBER OF SEQUENCES: 40

( 2 ) INFORMATION FOR SEQ ID NO:1:

( i ) SEQUENCE CHARACTERISTICS:
( A ) LENGTH: 1050 base pairs
( B ) TYPE: nucleic acid
( C ) STRANDEDNESS: double
( D ) TOPOLOGY: linear ( i i i ) HYPOTHETICAL: NO ( i v ) ANTI-SENSE: NO ( i x ) FEATURE:
( A ) NAME/KEY: CDS
( B ) LOCATION: 1..1050

( x i ) SEQUENCE DESCRIPTION: SEQ ID NO:1:

ATG GCA GCC GAT GCC CCG GGA GAC CGG ATG GAG GAG CCC CTG CCA GAC 48
Met Ala Ala Asp Ala Pro Gly Asp Arg Met Glu Glu Pro Leu Pro Asp
1 5 10 15

AGG GCC GTG CCC ATT TAC GTG GCT GGG TTT TTG GCC CTG TAT GAC AGC 96
Arg Ala Val Pro Ile Tyr Val Ala Gly Phe Leu Ala Leu Tyr Asp Ser
20 25 30

GGG GAC TCG GGC GAG TTG GCA TTG GAT CCG GAT ACG GTG CGT GCG GCC 144
Gly Asp Ser Gly Glu Leu Ala Leu Asp Pro Asp Thr Val Arg Ala Ala
35 40 45

CTG CCT CCG GAT AAC CCA CTC CCG ATT AAC GTG GAC CAC CGC GCT GGC 192
Leu Pro Pro Asp Asn Pro Leu Pro Ile Asn Val Asp His Arg Ala Gly
50 55 60

TGC GAG GTG GGG CGG GTG CTG GCC GTG GTC GAC GAC CCC CGC GGG CCG 240
Cys Glu Val Gly Arg Val Leu Ala Val Val Asp Asp Pro Arg Gly Pro
65 70 75 80

TTT TTT GTG GGA CTG ATC GCC TGC GTG CAA CTG GAG CGC GTC CTC GAG 288
Phe Phe Val Gly Leu Ile Ala Cys Val Gln Leu Glu Arg Val Leu Glu
85 90 95

ACG GCC GCC AGC GCT GCG ATT TTC GAG CGC CGC GGG CCG CCG CTC TCC 336
Thr Ala Ala Ser Ala Ala Ile Phe Glu Arg Arg Gly Pro Pro Leu Ser
100 105 110

CGG GAG GAG CGC CTG TTG TAC CTG ATC ACC AAC TAC CTG CCC TCG GTC 384
Arg Glu Glu Arg Leu Leu Tyr Leu Ile Thr Asn Tyr Leu Pro Ser Val
115 120 125

TCC CTG GCC ACA AAA CGC CTG GGG GGC GAG GCG CAC CCC GAT CGC ACG 432
Ser Leu Ala Thr Lys Arg Leu Gly Gly Glu Ala His Pro Asp Arg Thr
130 135 140

CTG TTC GCG CAC GTC GCG CTG TGC GCG ATC GGG CGG CGC CTC GGC ACT 480
Leu Phe Ala His Val Ala Leu Cys Ala Ile Gly Arg Arg Leu Gly Thr
145 150 155 160

ATC GTC ACC TAC GAC ACC GGT CTC GAC GCC GCC ATC GCG CCC TTT CGC 528
Ile Val Thr Tyr Asp Thr Gly Leu Asp Ala Ala Ile Ala Pro Phe Arg
165 170 175

CAC CTG TCG CCG GCG TCT CGC GAG GGG GCG CGG CGA CTG GCC GCC GAG 576
His Leu Ser Pro Ala Ser Arg Glu Gly Ala Arg Arg Leu Ala Ala Glu
180 185 190

GCC GAG CTC GCG CTG TCC GGA CGC ACC TGG GCG CCC GGC GTG GAG GCG 624
Ala Glu Leu Ala Leu Ser Gly Arg Thr Trp Ala Pro Gly Val Glu Ala
195 200 205

CTG ACC CAC ACG CTG CTT TCC ACC GCC GTT AAC AAC ATG ATG CTG CGG 672
Leu Thr His Thr Leu Leu Ser Thr Ala Val Asn Asn Met Met Leu Arg
210 215 220

GAC CGC TGG AGC CTG GTG GCC GAG CGG CGG CGG CAG GCC GGG ATC GCC 720
Asp Arg Trp Ser Leu Val Ala Glu Arg Arg Arg Gln Ala Gly Ile Ala
225 230 235 240

GGA CAC ACC TAC CTC CAG GCG AGC GAA AAA TTC AAA ATG TGG GGG GCG 768
Gly His Thr Tyr Leu Gln Ala Ser Glu Lys Phe Lys Met Trp Gly Ala
245 250 255

GAG CCT GTT TCC GCG CCG GCG CGC GGG TAT AAG AAC GGG GCC CCG GAG 816
Glu Pro Val Ser Ala Pro Ala Arg Gly Tyr Lys Asn Gly Ala Pro Glu
260 265 270

TCC ACG GAC ATA CCG CCC GGC TCG ATC GCT GCC GCG CCG CAG GGT GAC 864

-continued

Ser Thr Asp Ile Pro Pro Gly Ser Ile Ala Ala Ala Pro Gln Gly Asp
275 280 285

CGG TGC CCA ATC GTC CGT CAG CGC GGG GTC GCC TCG CCC CCG GTA CTG 912
Arg Cys Pro Ile Val Arg Gln Arg Gly Val Ala Ser Pro Pro Val Leu
290 295 300

CCC CCC ATG AAC CCC GTT CCG ACA TCG GGC ACC CCG GCC CCC GCG CCG 960
Pro Pro Met Asn Pro Val Pro Thr Ser Gly Thr Pro Ala Pro Ala Pro
305 310 315 320

CCC GGC GAC GGG AGC TAC CTG TGG ATC CCG GCC TCC CAT TAC AAC CAG 1008
Pro Gly Asp Gly Ser Tyr Leu Trp Ile Pro Ala Ser His Tyr Asn Gln
325 330 335

CTC GTC GCC GGC CAC GCC GCG CCC CAA CCC CAG CCG CAT TCC 1050
Leu Val Ala Gly His Ala Ala Pro Gln Pro Gln Pro His Ser
340 345 350

( 2 ) INFORMATION FOR SEQ ID NO:2:

( i ) SEQUENCE CHARACTERISTICS:
( A ) LENGTH: 350 amino acids
( B ) TYPE: amino acid
( D ) TOPOLOGY: linear ( i i ) MOLECULE TYPE: protein ( x i ) SEQUENCE DESCRIPTION: SEQ ID NO:2:

Met Ala Ala Asp Ala Pro Gly Asp Arg Met Glu Glu Pro Leu Pro Asp
1 5 10 15

Arg Ala Val Pro Ile Tyr Val Ala Gly Phe Leu Ala Leu Tyr Asp Ser
20 25 30

Gly Asp Ser Gly Glu Leu Ala Leu Asp Pro Asp Thr Val Arg Ala Ala
35 40 45

Leu Pro Pro Asp Asn Pro Leu Pro Ile Asn Val Asp His Arg Ala Gly
50 55 60

Cys Glu Val Gly Arg Val Leu Ala Val Val Asp Asp Pro Arg Gly Pro
65 70 75 80

Phe Phe Val Gly Leu Ile Ala Cys Val Gln Leu Glu Arg Val Leu Glu
85 90 95

Thr Ala Ala Ser Ala Ala Ile Phe Glu Arg Arg Gly Pro Pro Leu Ser
100 105 110

Arg Glu Glu Arg Leu Leu Tyr Leu Ile Thr Asn Tyr Leu Pro Ser Val
115 120 125

Ser Leu Ala Thr Lys Arg Leu Gly Gly Glu Ala His Pro Asp Arg Thr
130 135 140

Leu Phe Ala His Val Ala Leu Cys Ala Ile Gly Arg Arg Leu Gly Thr
145 150 155 160

Ile Val Thr Tyr Asp Thr Gly Leu Asp Ala Ala Ile Ala Pro Phe Arg
165 170 175

His Leu Ser Pro Ala Ser Arg Glu Gly Ala Arg Arg Leu Ala Ala Glu
180 185 190

Ala Glu Leu Ala Leu Ser Gly Arg Thr Trp Ala Pro Gly Val Glu Ala
195 200 205

Leu Thr His Thr Leu Leu Ser Thr Ala Val Asn Asn Met Met Leu Arg
210 215 220

Asp Arg Trp Ser Leu Val Ala Glu Arg Arg Arg Gln Ala Gly Ile Ala
225 230 235 240

Gly His Thr Tyr Leu Gln Ala Ser Glu Lys Phe Lys Met Trp Gly Ala
245 250 255

Glu Pro Val Ser Ala Pro Ala Arg Gly Tyr Lys Asn Gly Ala Pro Glu

-continued

```
                260                                265                                270

Ser Thr Asp Ile Pro Pro Gly Ser Ile Ala Ala Ala Pro Gln Gly Asp
        275                 280                 285

Arg Cys Pro Ile Val Arg Gln Arg Gly Val Ala Ser Pro Pro Val Leu
    290                 295                 300

Pro Pro Met Asn Pro Val Pro Thr Ser Gly Thr Pro Ala Pro Ala Pro
305                 310                 315                 320

Pro Gly Asp Gly Ser Tyr Leu Trp Ile Pro Ala Ser His Tyr Asn Gln
                325                 330                 335

Leu Val Ala Gly His Ala Ala Pro Gln Pro Gln Pro His Ser
            340                 345                 350
```

( 2 ) INFORMATION FOR SEQ ID NO:3:

( i ) SEQUENCE CHARACTERISTICS:
( A ) LENGTH: 7 base pairs
( B ) TYPE: nucleic acid
( C ) STRANDEDNESS: single
( D ) TOPOLOGY: linear ( i i i ) HYPOTHETICAL: NO ( i v ) ANTI-SENSE: NO ( x i ) SEQUENCE DESCRIPTION: SEQ ID NO:3:

GAATGCN 7

( 2 ) INFORMATION FOR SEQ ID NO:4:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i i ) HYPOTHETICAL: NO ( i v ) ANTI-SENSE: NO ( x i ) SEQUENCE DESCRIPTION: SEQ ID NO:4:

GTACTCAAAA GGTCATAC 18

( 2 ) INFORMATION FOR SEQ ID NO:5:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i i ) HYPOTHETICAL: NO ( i v ) ANTI-SENSE: NO ( x i ) SEQUENCE DESCRIPTION: SEQ ID NO:5:

GGGAAACCAA ACGCGGAATG 20

( 2 ) INFORMATION FOR SEQ ID NO:6:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i i ) HYPOTHETICAL: NO ( i v ) ANTI-SENSE: NO -continued ( x i ) SEQUENCE DESCRIPTION: SEQ ID NO:6:

GATACGGTGC GGGCAGTACT GCCTCCGGAT 30

( 2 ) INFORMATION FOR SEQ ID NO:7:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i i ) HYPOTHETICAL: NO ( i v ) ANTI-SENSE: NO ( x i ) SEQUENCE DESCRIPTION: SEQ ID NO:7:

ATCCGGAGGC AGTACTGCCC GCACCGTATC 30

( 2 ) INFORMATION FOR SEQ ID NO:8:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i i i ) HYPOTHETICAL: NO ( i v ) ANTI-SENSE: NO ( x i ) SEQUENCE DESCRIPTION: SEQ ID NO:8:

TTTTTGGCGC TCTTCGACAG CGGGGAC 27

( 2 ) INFORMATION FOR SEQ ID NO:9:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i i i ) HYPOTHETICAL: NO ( i v ) ANTI-SENSE: NO ( x i ) SEQUENCE DESCRIPTION: SEQ ID NO:9:

GTCCCCGCTG TCGAAGAGCG CCAAAAA 27

( 2 ) INFORMATION FOR SEQ ID NO:10:

( i ) SEQUENCE CHARACTERISTICS:
( A ) LENGTH: 12 base pairs
( B ) TYPE: nucleic acid
( C ) STRANDEDNESS: single
( D ) TOPOLOGY: linear ( i i i ) HYPOTHETICAL: NO ( i v ) ANTI-SENSE: NO ( x i ) SEQUENCE DESCRIPTION: SEQ ID NO:10:

CATGATTAAT TA 12

( 2 ) INFORMATION FOR SEQ ID NO:11:

( i ) SEQUENCE CHARACTERISTICS:
( A ) LENGTH: 12 base pairs
( B ) TYPE: nucleic acid
( C ) STRANDEDNESS: single -continued ( D ) TOPOLOGY: linear ( i i i ) HYPOTHETICAL: NO ( i v ) ANTI-SENSE: NO ( x i ) SEQUENCE DESCRIPTION: SEQ ID NO:11:

AGCTTAATTA AT 12

( 2 ) INFORMATION FOR SEQ ID NO:12:

( i ) SEQUENCE CHARACTERISTICS:
( A ) LENGTH: 43 base pairs
( B ) TYPE: nucleic acid
( C ) STRANDEDNESS: single
( D ) TOPOLOGY: linear ( i i i ) HYPOTHETICAL: NO ( i v ) ANTI-SENSE: NO ( x i ) SEQUENCE DESCRIPTION: SEQ ID NO:12:

CCCACTCCCG ATTAACGTGG ACGTCCGCGC TGGCTGCGAG GTG 43

( 2 ) INFORMATION FOR SEQ ID NO:13:

( i ) SEQUENCE CHARACTERISTICS:
( A ) LENGTH: 41 base pairs
( B ) TYPE: nucleic acid
( C ) STRANDEDNESS: single
( D ) TOPOLOGY: linear ( i i i ) HYPOTHETICAL: NO ( i v ) ANTI-SENSE: NO ( x i ) SEQUENCE DESCRIPTION: SEQ ID NO:13:

CCTCGCAGCC AGCGCGGACG TCCACGTTAA TCGGGAGTGG G 41

( 2 ) INFORMATION FOR SEQ ID NO:14:

( i ) SEQUENCE CHARACTERISTICS:
( A ) LENGTH: 49 base pairs
( B ) TYPE: nucleic acid
( C ) STRANDEDNESS: single
( D ) TOPOLOGY: linear ( i i i ) HYPOTHETICAL: NO ( i v ) ANTI-SENSE: NO ( x i ) SEQUENCE DESCRIPTION: SEQ ID NO:14:

CCCCGATCGC ACGCTGTTCG CTGCAGTCGC GCTGTGCGCG ATCGGGCGG 49

( 2 ) INFORMATION FOR SEQ ID NO:15:

( i ) SEQUENCE CHARACTERISTICS:
( A ) LENGTH: 43 base pairs
( B ) TYPE: nucleic acid
( C ) STRANDEDNESS: single
( D ) TOPOLOGY: linear ( i i i ) HYPOTHETICAL: NO ( i v ) ANTI-SENSE: NO ( x i ) SEQUENCE DESCRIPTION: SEQ ID NO:15:

GATCGCGCAC AGCGCGACTG CAGCGAACAG CGTGCGATCG GGG 43

( 2 ) INFORMATION FOR SEQ ID NO:16:

-continued ( i ) SEQUENCE CHARACTERISTICS:
( A ) LENGTH: 48 base pairs
( B ) TYPE: nucleic acid
( C ) STRANDEDNESS: single
( D ) TOPOLOGY: linear ( i i i ) HYPOTHETICAL: NO ( i v ) ANTI-SENSE: NO ( x i ) SEQUENCE DESCRIPTION: SEQ ID NO:16:

CACCAACTAC CTGCCCTCGG TCGCGCTAGC CACAAAACGC CTGGGGGG 48

( 2 ) INFORMATION FOR SEQ ID NO:17:

( i ) SEQUENCE CHARACTERISTICS:
( A ) LENGTH: 40 base pairs
( B ) TYPE: nucleic acid
( C ) STRANDEDNESS: single
( D ) TOPOLOGY: linear ( i i i ) HYPOTHETICAL: NO ( i v ) ANTI-SENSE: NO ( x i ) SEQUENCE DESCRIPTION: SEQ ID NO:17:

CAGGCGTTTT GTGGCTAGCG CGACCGAGGG CAGGTAGTTG 40

( 2 ) INFORMATION FOR SEQ ID NO:18:

( i ) SEQUENCE CHARACTERISTICS:
( A ) LENGTH: 44 base pairs
( B ) TYPE: nucleic acid
( C ) STRANDEDNESS: single
( D ) TOPOLOGY: linear ( i i i ) HYPOTHETICAL: NO ( i v ) ANTI-SENSE: NO ( x i ) SEQUENCE DESCRIPTION: SEQ ID NO:18:

CCAACTACCT GCCCTCGGTC GCCCTGGCCA CAAAACGCCT GGGG 44

( 2 ) INFORMATION FOR SEQ ID NO:19:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i i ) HYPOTHETICAL: NO ( i v ) ANTI-SENSE: NO ( x i ) SEQUENCE DESCRIPTION: SEQ ID NO:19:

GCCAGGGCGA CCGAGGG 17

( 2 ) INFORMATION FOR SEQ ID NO:20:

( i ) SEQUENCE CHARACTERISTICS:
( A ) LENGTH: 43 base pairs
( B ) TYPE: nucleic acid
( C ) STRANDEDNESS: single
( D ) TOPOLOGY: linear ( i i i ) HYPOTHETICAL: NO ( i v ) ANTI-SENSE: NO ( x i ) SEQUENCE DESCRIPTION: SEQ ID NO:20:

-continued

CCCACTCCCG ATTAACGTGG ACTACCGCGC TGGCTGCGAG GTG 43

( 2 ) INFORMATION FOR SEQ ID NO:21:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i i ) HYPOTHETICAL: NO ( i v ) ANTI-SENSE: NO ( x i ) SEQUENCE DESCRIPTION: SEQ ID NO:21:

CGCGGTAGTC CACGTTA 17

( 2 ) INFORMATION FOR SEQ ID NO:22:

( i ) SEQUENCE CHARACTERISTICS:
( A ) LENGTH: 45 base pairs
( B ) TYPE: nucleic acid
( C ) STRANDEDNESS: single
( D ) TOPOLOGY: linear ( i i i ) HYPOTHETICAL: NO ( i v ) ANTI-SENSE: NO ( x i ) SEQUENCE DESCRIPTION: SEQ ID NO:22:

CCCCGATCGC ACGCTGTTCG CGTACGTCGC GCTGTGCGCG ATCGG 45

( 2 ) INFORMATION FOR SEQ ID NO:23:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i i ) HYPOTHETICAL: NO ( i v ) ANTI-SENSE: NO ( x i ) SEQUENCE DESCRIPTION: SEQ ID NO:23:

GCGACGTACG CGAACAGC 18

( 2 ) INFORMATION FOR SEQ ID NO:24:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( i i i ) HYPOTHETICAL: NO ( i v ) ANTI-SENSE: NO ( x i ) SEQUENCE DESCRIPTION: SEQ ID NO:24:

CACCAACTAC GTGCCCTCGG TCTCCCTG 28

( 2 ) INFORMATION FOR SEQ ID NO:25:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear -continued ( i i i ) HYPOTHETICAL: NO ( i v ) ANTI-SENSE: NO ( x i ) SEQUENCE DESCRIPTION: SEQ ID NO:25:

CCGAGGGCAC GTAGTTGGTG ATCAGG 26

( 2 ) INFORMATION FOR SEQ ID NO:26:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( i i i ) HYPOTHETICAL: NO ( i v ) ANTI-SENSE: NO ( x i ) SEQUENCE DESCRIPTION: SEQ ID NO:26:

CAACTACCTG GGCTCGGTCT CCCTGGCC 28

( 2 ) INFORMATION FOR SEQ ID NO:27:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( i i i ) HYPOTHETICAL: NO ( i v ) ANTI-SENSE: NO ( x i ) SEQUENCE DESCRIPTION: SEQ ID NO:27:

GAGACCGAGC CCAGGTAGTT GGTGATCAG 29

( 2 ) INFORMATION FOR SEQ ID NO:28:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( i i i ) HYPOTHETICAL: NO ( i v ) ANTI-SENSE: NO ( x i ) SEQUENCE DESCRIPTION: SEQ ID NO:28:

CGCTGTTCGC ACGCGTCGCG CTGTGCGCGA TCG 33

( 2 ) INFORMATION FOR SEQ ID NO:29:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( i i i ) HYPOTHETICAL: NO ( i v ) ANTI-SENSE: NO ( x i ) SEQUENCE DESCRIPTION: SEQ ID NO:29:

CAGCGCGACG CGTGCGAACA GCGTGCGATC GGG 33

( 2 ) INFORMATION FOR SEQ ID NO:30:

( i ) SEQUENCE CHARACTERISTICS:

-continued ( A ) LENGTH: 32 base pairs
( B ) TYPE: nucleic acid
( C ) STRANDEDNESS: single
( D ) TOPOLOGY: linear ( i i i ) HYPOTHETICAL: NO ( i v ) ANTI-SENSE: NO ( x i ) SEQUENCE DESCRIPTION: SEQ ID NO:30:

CTGTTCGCGG AAGTAGCGCT GTGCGCGATC GG 32

( 2 ) INFORMATION FOR SEQ ID NO:31:

( i ) SEQUENCE CHARACTERISTICS:
( A ) LENGTH: 37 base pairs
( B ) TYPE: nucleic acid
( C ) STRANDEDNESS: single
( D ) TOPOLOGY: linear ( i i i ) HYPOTHETICAL: NO ( i v ) ANTI-SENSE: NO ( x i ) SEQUENCE DESCRIPTION: SEQ ID NO:31:

CGCACAGCGC TACTTCCGCG AACAGCGTGC GATCGGG 37

( 2 ) INFORMATION FOR SEQ ID NO:32:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( i i i ) HYPOTHETICAL: NO ( i v ) ANTI-SENSE: NO ( x i ) SEQUENCE DESCRIPTION: SEQ ID NO:32:

CGCTGTTCGC CAAGGTCGCG CTGTGCGCGA TCG 33

( 2 ) INFORMATION FOR SEQ ID NO:33:

( i ) SEQUENCE CHARACTERISTICS:
( A ) LENGTH: 35 base pairs
( B ) TYPE: nucleic acid
( C ) STRANDEDNESS: single
( D ) TOPOLOGY: linear ( i i i ) HYPOTHETICAL: NO ( i v ) ANTI-SENSE: NO ( x i ) SEQUENCE DESCRIPTION: SEQ ID NO:33:

CACAGCGCGA CCTTGGCGAA CAGCGTGCGA TCGGG 35

( 2 ) INFORMATION FOR SEQ ID NO:34:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( i i i ) HYPOTHETICAL: NO ( i v ) ANTI-SENSE: NO ( x i ) SEQUENCE DESCRIPTION: SEQ ID NO:34:

CCGATTAACG TTGACGCCCG CGCTGGCTGC GAGGTGGG 38

-continued ( 2 ) INFORMATION FOR SEQ ID NO:35:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( i i i ) HYPOTHETICAL: NO ( i v ) ANTI-SENSE: NO ( x i ) SEQUENCE DESCRIPTION: SEQ ID NO:35:

CAGCCAGCGC GGGCGTCAAC GTTAATCGGG AGTGGG 36

( 2 ) INFORMATION FOR SEQ ID NO:36:

( i ) SEQUENCE CHARACTERISTICS:
( A ) LENGTH: 35 base pairs
( B ) TYPE: nucleic acid
( C ) STRANDEDNESS: single
( D ) TOPOLOGY: linear ( i i i ) HYPOTHETICAL: NO ( i v ) ANTI-SENSE: NO ( x i ) SEQUENCE DESCRIPTION: SEQ ID NO:36:

CCTGCCCTCG GTAAGCTTGG CCACAAAACG CCTGG 35

( 2 ) INFORMATION FOR SEQ ID NO:37:

( i ) SEQUENCE CHARACTERISTICS:
( A ) LENGTH: 35 base pairs
( B ) TYPE: nucleic acid
( C ) STRANDEDNESS: single
( D ) TOPOLOGY: linear ( i i i ) HYPOTHETICAL: NO ( i v ) ANTI-SENSE: NO ( x i ) SEQUENCE DESCRIPTION: SEQ ID NO:37:

GGCGTTTTGT GGCCAAGCTT ACCGAGGGCA GGTAG 35

( 2 ) INFORMATION FOR SEQ ID NO:38:

( i ) SEQUENCE CHARACTERISTICS:
( A ) LENGTH: 16 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO:38:

Asp Ala Pro Gly Asp Arg Met Glu Glu Pro Leu Pro Asp Arg Ala Cys
1 5 10 15

( 2 ) INFORMATION FOR SEQ ID NO:39:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear -continued ( i i i ) HYPOTHETICAL: NO ( i v ) ANTI-SENSE: NO ( x i ) SEQUENCE DESCRIPTION: SEQ ID NO:39:

CGTATCCGGA TCCAATC 17

( 2 ) INFORMATION FOR SEQ ID NO:40:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i i ) HYPOTHETICAL: NO ( i v ) ANTI-SENSE: NO ( x i ) SEQUENCE DESCRIPTION: SEQ ID NO:40:

GTTAACAACA TGATGCTG 18

METHOD OF MAKING HERPES SIMPLEX TYPE 1 MUTANTS AND MUTANTS SO PRODUCED

DESCRIPTION OF THE INVENTION

This invention relates to a method for the introduction of mutations into a specific portion of the Herpes Simplex Virus type 1 (HSV-1) virus, particularly into its protease gene, and to mutant viruses so produced.

BACKGROUND OF THE INVENTION

The Herpes Simplex Type-1 (HSV-1) virus is a relatively large virus (152,260 bp). While much is known about the viral life cycle and its general activity, it has been difficult to study the relationship between biochemical and biophysiological properties of its gene products and the viral life cycle, since its large size makes it difficult to create predetermined point mutations.

HSV-1 protease is a serine protease that has both a structural and enzymatic role in the assembly of the HSV-1 capsid. The protease and infected cell protein 35 (ICP-35) form a complex of approximately 1100 molecules in a ratio of 1:10 within the nucleus of the infected cell. Around this complex the capsid proteins assemble into B capsids. After assembly the protease cleaves itself twice and ICP-35 once, releasing the ICP-35 and the carboxyl terminal fragment of the protease from the capsid interior. The 247 amino acid protease remains within the capsid. Concurrently (or subsequently) the genomic HSV-1 DNA is packaged within the capsid.

It would be desirable to have a simplified method of obtaining predetermined mutations in the HSV virus.

DETAILED DESCRIPTION OF THE INVENTION

This invention relates to a method of making a mutated HSV-1 virus, wherein the mutation comprises a mutation selected from the group of: point mutations within a gene, an insertion of DNA, a deletion of DNA, and combinations thereof comprising transforming a host cell with a set of vectors comprising:

a first vector comprising a section of the HSV-1 genome comprising the mutation and overlapping DNA homologous with overlapping DNA of at least one additional vector; and additional vectors, each additional vector comprising a fragment of the substantially complete HSV-1 genome and also comprising overlapping DNA which is homologous with a sequential genomic fragment contained in at least one additional vector, so that upon transfection of a host cell, replication of viral DNA and recombination of viral DNA, a mutated virus which is replicable in a wild type or host range cell line is formed.

This invention further relates to a method of making an HSV-1 virus having a mutated gene comprising transforming a host cell with a set of vectors comprising:

a first vector comprising a mutated HSV-1 gene and overlapping DNA homologous with overlapping DNA of at least one additional vector; and additional vectors, each additional vector comprising a fragment of the substantially complete HSV-1 genome and also comprising overlapping DNA which is homologous with a sequential genomic fragment contained in at least one other additional vector, so that upon co-transfection of a host cell, replication of viral DNA, and recombination of viral DNA, a virus is formed which is replicable in a wild type or host range cell line.

This invention further relates to a method of making an HSV-1 virus having a mutated gene comprising the steps of:

(a) obtaining a set of starting vectors, each starting vector comprising a fragment of the substantially complete HSV-1 genome and also comprising overlapping DNA which is homologous with a sequential genomic fragment contained in at least one other starting vector, so that upon co-transfection of a host cell, replication of viral DNA, and recombination of viral DNA, a virus is formed which is replicable in a wild type or host range cell line;

(b) replacing a starting vector comprising a gene which is to be mutated with: a first replacement vector comprising a mutated gene and overlapping DNA, and at least one additional replacement vector comprising genomic DNA which was present in the replaced starting vector, but is not present in the first replacement vector and overlapping DNA; and (c) co-transfecting a host cell with the replacement vectors and the remaining starting vectors under conditions allowing replication of viral DNA and recombination of viral DNA to form a mutated virus which is replicable in a wild type or host range cell line.

The first replacement vector may be made by a process comprising:

(a) creating a vector comprising a gene site which is to be mutated and overlapping DNA;

(b) defining a first restriction endonuclease site in a position 5' to the gene site which is to be mutated;

(c) defining a second restriction endonuclease site in a position 3' to the gene site which is to be mutated, to define a wild-type gene segment contained between the first and second restriction endonuclease sites;

(d) creating a mutant gene segment substantially identical to the wild-type gene segment, except for comprising a desired mutation;

(e) replacing the wild-type gene segment with the mutant gene segment to obtain the first replacement vector.

A further aspect of this invention is a set of vectors comprising: a first vector comprising a mutated HSV-1 and overlapping DNA homologous with overlapping DNA of at least one additional vector; and additional vectors, each additional vector comprising a fragment of the substantially complete HSV-I genome and also comprising overlapping DNA which is homologous with a sequential genomic fragment contained in at least one other additional vector, so that upon co-transfection of a host cell, replication of viral DNA, and recombination of viral DNA, a mutated virus is formed which is replicable in a wild type or host range cell line.

A further aspect of this invention are mutant viruses which can be made by the methods and using the vectors described above.

This invention also relates to a method of making an HSV-1 virus having a mutated protease gene by transforming a host cell with a set of vectors comprising: a first vector comprising a HSV-1 mutant protease gene and overlapping DNA homologous with overlapping DNA of at least one additional vector; and additional vectors, each additional vector comprising a fragment of the substantially complete HSV-1 genome and also comprising overlapping DNA which is homologous with a sequential genomic fragment contained in at least one other additional vector, so that upon co-transfection of a host cell, replication of viral DNA, and recombination, a virus having a mutated protease gene and which is replicable in a wild type or host range cell line is formed.

This invention also relates to a method of making a mutant HSV-1 encoding a mutant viral protease comprising the steps of:

(a) obtaining a set of starting vectors, each starting vector comprising a fragment of the substantially complete HSV-1 genome and also comprising DNA which is overlapping DNA with a sequential genomic fragment contained in other starting vectors, so that upon co-transfection of a host cell, replication of viral DNA, and recombination of viral DNA, a virus which is replicable in a wild type or host range cell line is formed;

(b) replacing a starting vector comprising a protease gene which is to be mutated with: a first replacement vector comprising a full length mutated protease gene and overlapping DNA, and at least one additional replacement vector comprising genomic DNA which was present in the replaced starting vector, but is not present in the first replacement vector and overlapping DNA; and (c) co-transfecting a host cell with the replacement vectors and the remaining starting vectors under conditions allowing replication of viral DNA and recombination of viral DNA to form a mutant virus which is replicable in a wild type or host range cell line.

The first replacement vector may be made by a process comprising:

(a) creating a vector comprising a protease gene site which is to be mutated and overlapping DNA;

(b) defining a first restriction endonuclease site in a position 5' to the protease gene segment which is to be mutated;

(c) defining a second restriction endonuclease site in a position 3' to the protease gene site which is to be mutated to define a wild-type protease gene segment contained between the first and second restriction endonuclease sites;

(d) creating a mutant protease gene segment substantially identical to the wild-type gene segment, except for comprising a desired mutation; and (e) replacing the wild-type gene segment with the mutant protease gene segment to obtain the first replacement vector.

In addition to creating desired point mutations, the process of this invention allows one to make any other desired mutations, such as the deletion of an existing HSV-1 DNA segment, or the insertion of extra DNA, regardless of source into an HSV-1. Thus throughout the specification and claims, the terms "mutated" and "mutant" should be given their broadest meanings.

Thus this invention further comprises a process for making a mutated HSV-1 virus wherein the mutation comprises an insertion of DNA comprising transforming a host cell with a set of vectors comprising:

a first vector comprising DNA to be inserted, and overlapping DNA homologous with overlapping DNA of at least one additional vector; and additional vectors, each additional vector comprising a fragment of the substantially complete HSV-1 genome and also comprising overlapping DNA which is homologous with a sequential genomic fragment contained in at least one additional vector so that upon co-transfection of a host cell, replication of viral DNA, and homologous recombination a mutated virus which is replicable in a wild type or host range cell line is formed. Vectors carrying the DNA to be inserted may be made substantially as those described carrying point mutations.

Additionally, this invention also comprises a process for making a mutated HSV-1 virus wherein the mutation comprises a deletion of DNA comprising transforming a host cell with a set of vectors comprising:

a first vector comprising DNA homologous to DNA flanking the DNA which is to be deleted, and overlapping DNA homologous with overlapping DNA of at least one additional vector; and additional vectors, each additional vector comprising a fragment of the substantially complete HSV-1 genome and also overlapping DNA which is homologous with a sequential genomic fragment contained in at least one additional vector, so that upon co-transfection of a host cell, replication of vital DNA, and homologous recombination, a mutated virus which is replicable in a wild type or host range cell line is formed. Vectors may be made substantially as described for the point mutations.

A further aspect of this invention are mutant viruses which can be made by the method described above. Preferred mutant viruses of this invention contain altered protease genes which coffer phenotypes which are different from the wild-type virus.

BRIEF DESCRIPTION OF THE FIGURES

FIG. 1 is the DNA and amino acid sequences (SEQ.ID.NOS 1 and 2) of the HSV-I(F) protease (Pra) BsmI fragment. (The 82bp upstream fragment is not shown).

FIG. 3 is a diagram of the plasmid/cosmid-based mutagenesis process of this invention.

Figure 2:
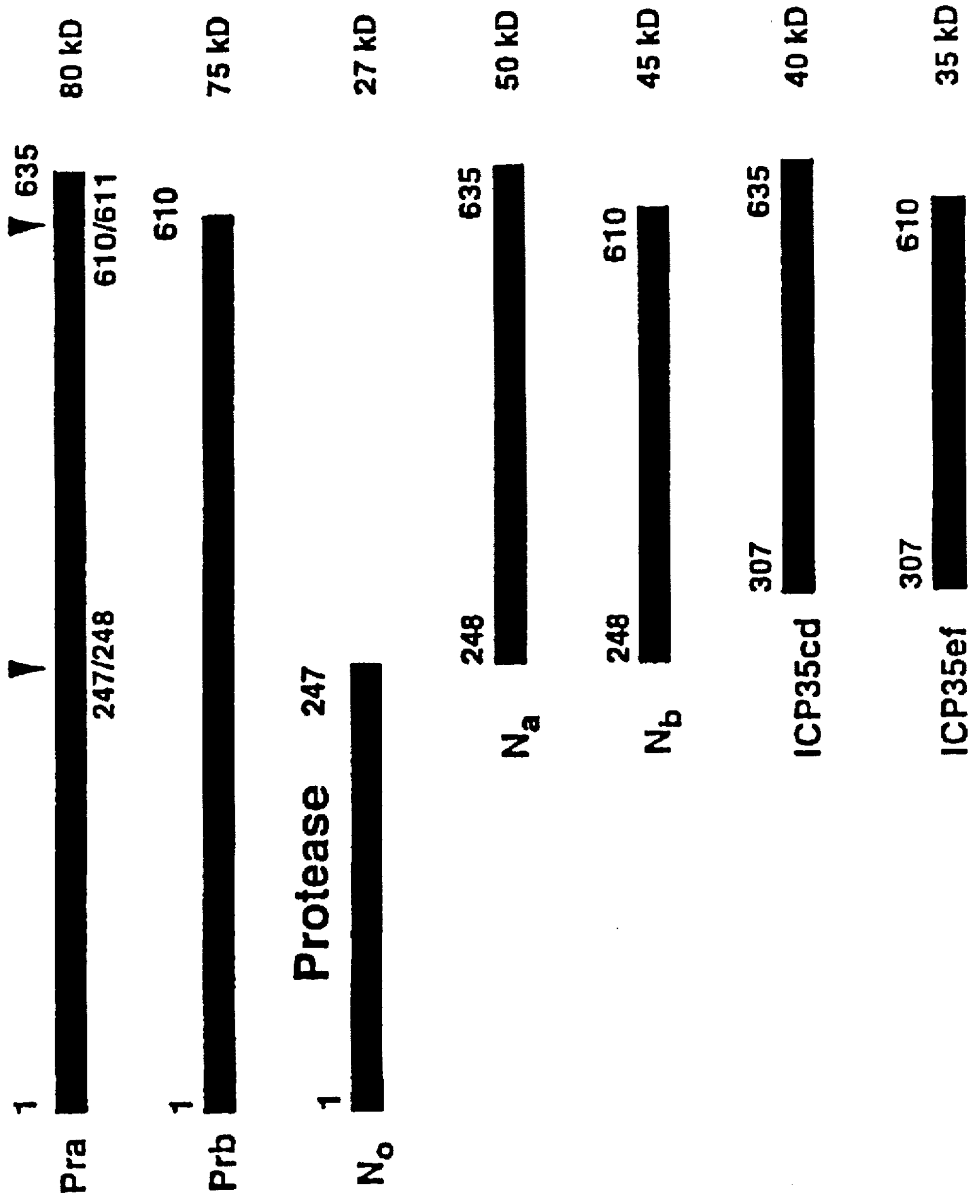
FIG. 2 shows the cleavage sites for HSV-1 protease (Pra). Pra is a 635 amino acid serine protease that undergoes autocatalytic cleavage at Ala247 and Ala610. Products of the cleavage are diagrammed.

As used in the specification and claims, the following definitions apply:

Null Mutant: an HSV-1 mutant which lacks the ability to grow or form plaques on Veto cells.

Overlapping Vectors: two or more vectors, each containing a segment of a DNA which has sufficient common base pairs with the DNA contained in a second vector so that homologous recombination can occur when copies of the DNA are present in a common host.

Replacement Vector: a vector, generally a plasmid, which contains a portion of a HSV-1 genomic fragment which was originally present in a starting vector. In preferred embodiments, a starting vector will be replaced by two replacement vectors: the first one comprising the full length mutant gene and the second one comprising the remaining genomic DNA which was contained in the starting vector, but not present in the first vector. Additionally, replacement vectors also contain sufficient overlapping DNA so that homologous recombination can occur.

Starting Vector: one of a series of vectors, generally cosmids, which together contain the full length genomic DNA of HSV-1 along with overlapping DNA.

Overlapping DNA: a segment of DNA at least about 300 base pairs in length, more preferably about 2,000 to 5,000 base pairs in length, which is substantially identical to a segment in another vector. The vector generally contains two differing overlapping DNAs: one on the 5' end of the HSV-1 genomic DNA and one on the 3' end of the HSV-1 genomic DNA, and each overlapping DNA overlaps that of a different vector.

Host Range Cell line: a host cell line which has been transformed to express a viral gene. Viruses which do not produce a functional version of this gene are able to utilize the protein that is produced by the transformed cell line. In preferred embodiments, the host range cell line expresses HSV-I protease.

Substantially Complete Genome: sufficient DNA is present so that upon transfection of a host cell, replication of the viral DNA and homologous recombination, a replicable HSV-1 virus is formed. This invention specifically envisions: 1) a HSV-1 virus containing a complete genome containing desired mutations and 2) an HSV-1 virus which does not have a complete genome, but the genes which are missing are not essential for virus replication; 3) an HSV-1 virus which is missing gene(s) essential for virus replication, but the missing gene product(s) are complemented by those produced in a host range cell line; and 4) an HSV-1 virus according to 1) or 2) or 3) and/or comprises additional DNA, regardless of source, which does not interfere with virus replication, or if replication is interfered with, which can be complemented by a host range cell line.

Replicable Virus: an HSV-I virus whose genome is neither too short not too long, so that functional capsid assembly and packaging occurs.

One aspect of this invention is a convenient system which allows researchers to study any single gene in the context of the virus, and to create any desired mutation(s) within the virus, including insertions (regardless of the source of the DNA insert) and deletions.

The starting point for the method according to this invention is a set of vectors, such as cosmids. The total number of vectors in the set is not critical, but together the set of vectors contain a substantially complete HSV-1 genome. In general, the total number of vectors should not be so large that it becomes cumbersome to co-transfect the host cell. Preferably, the number of vectors in a set should be less than ten, and more preferably, less than about eight, and most preferably about six.

One or more of the vectors in the set are replaced by one or more replacement vectors, each replacement vector containing a smaller HSV-1 DNA insert than was present in the starting vector, but together the replacement vectors contain the "equivalent amount" of unique, non-overlapping HSV-1 genomic DNA as was present in the starting vector. ("Equivalent amount" as used in this context means substantially the same amount, plus or minus any DNA which was intentionally added or deleted as mutations.) If the complete gene which is to be mutated is contained within one starting vector, then only this single vector needs to be replaced. If, however, the gene which is to be mutated is contained on two starting vectors (i.e., each starting vector contains only a fragment of the gene), then the two starting vectors should be replaced.

The first replacement vector of this invention may be a cosmid or a plasmid; plasmids are generally preferred. The vector may be any vector which is able to replicate in the host cell system. Any host cell may be utilized, but for general convenience, *E. coli* is preferred. The first replacement vector comprises a copy of the gene which one wishes to mutate, the DNA which is to be inserted along with DNA flanking the insertion point, or if the mutation is a deletion, DNA flanking the DNA which is to be deleted; the first replacement vector also comprises a sufficient amount of overlapping DNA so that homologous recombination can occur. While homologous recombination can occur with a few base pairs (i.e. less than 20), it is preferred that at least about 300 base pairs of overlapping DNA be present, and even more preferred that at least about 2,000 to about 5,000 be present. It is preferred that DNA be overlapping with DNA of at least one vector, and it is particularly preferred that it overlaps DNA of two vectors. Additional replacement vectors of this invention contain the remaining genes and/or gene fragments which were originally in the starting vector, along with overlapping DNA.

Next, two restrictions sites should be defined in the replacement vector when it contains a gene to be mutated. These restriction sites, which may be naturally occurring or may be inserted as desired using known techniques, define a gene fragment which can be replaced by a newly synthesized mutated gene fragment. The first restriction site may be anywhere upstream of the position where the mutation or mutations are to be introduced. In a preferred embodiment, it is upstream of the initiation ATG site of the structural gene which is to be mutated. The second restriction site may be anywhere within the gene, or even downstream of the gene, as long as it is downstream of the site where desired mutation or mutations are to be made. It is also desirable to choose a position for the second restriction site which is close enough to the first restriction site so that with currently available technology, a mutated gene fragment may be easily synthesized and sequenced as needed. Thus, the second restriction site is generally less than about 2,000 bp downstream of the first restriction site, and preferably less than about 1,100 bp downstream of the first restriction site.

The restriction sites may be the recognition sites for virtually any restriction endonuclease. It is preferred, however, that each site be unique. In order to ensure that the mutated gene fragment is cloned into the restriction sites having the correct orientation (i.e. can be "force-cloned"), it is particularly preferred that the enzyme recognizes different base pair sequences, and that the first restriction site and the second restriction site be differing base pair sequences, although recognized by the same enzyme. Numerous enzymes are known to have this characteristic, including BsmI.

The second replacement vector according to this invention comprises any viral DNA which was originally encoded in the first starting vector, but is not present in the first replacement vector, along with sufficient overlapping sequences so that homologous recombination can occur.

The remaining vectors in the set of vectors according to this invention may be any vectors, such that when the complete set of vectors is co-transfected into host cells, they are able to recombine to form a mutated virus which is replicable in a wild type or host range cell line.

In a preferred embodiment of this invention, a set of starting vectors to be used are the five cosmids: cos28, cos6, cos14, cos48, and cos56, which were obtained from Dr. Andrew J. Davison. These cosmids and/or their equivalents can be made according to the description given in Cunningham and Davison, Virology 197:116–124 (1993), which is hereby incorporated by reference.

Figures 3A, 3B, 3C:
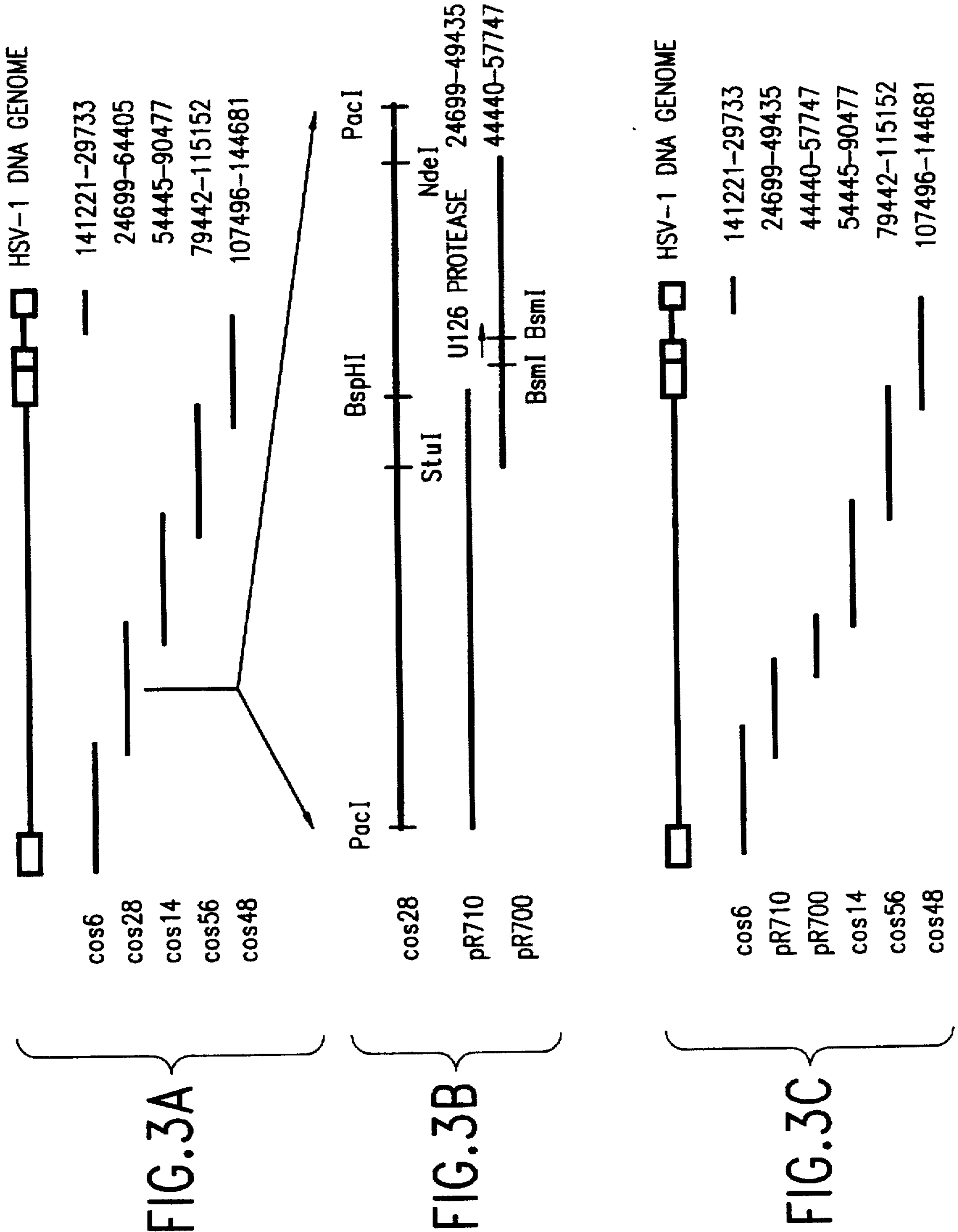
FIG. 3A illustrates five starting vectors (cos 6, cos 28, cos 14, cos 56, cos 48) that can be used in accordance with this invention.
FIG. 3B illustrates one of the cosmids (cos 28), containing DNA encoding the protease and its substrate (the assembly protein ICP-35) on the overlapping genes (UL26 and UL26.5), being replaced by two novel overlapping replacement vectors, plasmid pR700 and pR710.
FIG. 3C illustrates the two replacement plasmids and the four remaining starting vectors.

In one embodiment of this invention, the protease gene is to be mutated. Here, one of the cosmids of the Cunningham and Davison system, cosmid cos28, containing DNA encoding the protease and its substrate (the assembly protein ICP-35) on the overlapping genes CUL26 and UL26.5) is replaced by two novel overlapping replacement vectors, both of which are further aspects of this invention. This is diagrammed in FIG. 3B.

The first replacement vector should carry a copy of the HSV-1 protease gene which has at least two restriction sites that have been defined, according to the considerations mentioned above. One preferred restriction enzyme is BsmI, a degenerate restriction endonuclease with a recognition sequence of GAATG^CN^ (SEQ.ID.NO.:3).

In a preferred embodiment of this invention, the first replacement vector is plasmid pR700 or a plasmid carrying the same inserts as pR700. Plasmid pR700, was made from the commercially available plasmid pGEM-4Z (Promega Corp., Madison, Wis.), and contains the UL26 protease gene in a 13.3 kb insert of HSV-1 (base pairs 44440-57747). Plasmid pR700 also contains two naturally occurring BsmI sites, a first one 82 base pairs 5' of the HSV-1 protease start site and one at amino acid 348 of the protease. The "N" at the 5' BsmI site is "T" whereas at the 3' BsmI site, the "N" is "G", so that the mutant PCR fragments may be force-cloned into the vector. PCR mutagenesis of this 1.1 kb BsmI fragment was used to introduce various desired mutations into the HSV-1 protease gene fragment A preferred second replacement vector according to this invention is plasmid pR710, (or a plasmid carrying the same inserts as pR710) which is derived from commercially available plasmid pNEB93 (New England Biolabs Beverly, Mass.). Plasmid pR710 contains a 24.7 kb insert of HSV-1 (base pairs 24699-49435) that does not include the HSV-1 protease.

The two replacement plasmids and four remaining starting vectors, which together make up a further aspect of this invention, are introduced into HSV-1 host cells. The HSV-1 host cell chosen is generally not a critical aspect of this invention. Generally, any cell in which HSV-1 can replicate is an appropriate host cell. Particularly preferred host cells are Vero cells. DNA which is replicated during the virus life cycle homologously recombines in the host cells to create the mutant HSV-1 viruses of this invention. This is illustrated in FIG. 3.

The mutagenesis method of this invention allows one to make the desired HSV-1 mutations in the virus in a short period of time, i.e. within about 2 weeks. It has the further advantage that pure mutant virus cultures are generated; there are no wild type background viruses in the transfections of Vero cells.

In creating the mutant gene fragments of this invention, virtually any known method of synthesizing and mutating DNA may be used. PCR mutagenesis is a preferred method. In performing the PCR mutagenesis of the target DNA, standard PCR techniques may be used in general, such as those described in H. Russell, 1990 "Recombinant PCR" in PCR Protocols (Innis, et at., Eds.) Academic Press, Inc. San Diego, Calif., pages 177–183, which is hereby incorporated by reference. However, since HSV-1 DNA is quite GC rich and if the region which is to be mutated is also high in GC content (as is the case with the protease gene) it is preferred that a higher than usual melting temperature be employed during the PCR cycle, preferably at least about 99° C. to maximize product formation. A second consideration with PCR mutagenesis in general is maintaining fidelity. While any suitable polymerase enzyme may be employed, $Vent_R$ DNA polymerase (commercially available from New England Biolabs) is a preferred polymerase for the PCR reactions used herein because of its proofreading ability and thermal stability at 99° C.

Virtually any mutation which is desired may be introduced using the PCR mutagenesis method. For instance, in order to obtain viruses which have altered phenotypes, it is desirable to change an amino acid sequence. Further type of mutations which are preferred are those which introduce new restriction endonuclease recognition sites.

In order to demonstrate the versatility of the mutation procedure of this invention, the following mutant viruses were made. These viruses are the subject of co-pending patent application Ser. No. 08/457,558, filed herewith, which is hereby incorporated by reference.

Throughout the specification and claims, the virus nomenclature is the same as that used for the replacement plasmid containing the mutation, except that the virus uses the prefix "V" and the replacement plasmid uses "pR".

TABLE 1

Representative protease mutants

| VIRUS | MUTATION | ADDED SITE* |
|---|---|---|
| V711 | His 61 to Val 61 | AatII |
| V730 | His 61 to Ala 61 | Psp1406I |
| V715 | His 61 to Tyr 61 | none |
| V717 | Leu 125 to Val 125 | BsaAI |
| V718 | Pro 126 to Gly 126 | BstXI |
| V713 | Ser 129 to Ala 129 | NheI |
| V714 | Ser 129 to Ala 129 | none |
| V712 | His 148 to Ala 148 | PstI |
| V716 | His 148 to Tyr 148 | none |
| V725 | His 148 to Arg 148 | MulI |
| V728 | His 148 to Glu 148 | Eco47III |
| V732** | Ala 129 to Ser 129 | HindIII |
| V729 | His 148 to Lys 148 | StyI |

*restriction endonuclease site
**back mutation of V713

The active site serine of HSV-1 protease has been previously identified by chemical mutation methods to be Ser129. Therefore, changes of amino acids at the active serine site and near the active serine site were of particular interest.

Mutations At Ser 129:

A mutation was made in HSV-1 protease gene to change the protease amino acid 129 Ser to Ala129. This virus is designated V713. Recombinant virus could only be rescued on a host range cell line, PHS-23 which expresses protease. When V713 was used to super-infect Vero cells, the Western analysis showed an accumulation of the 80 kD protease (Pra) along with several other peptides ranging in molecular weight from 29 kD to 75 kD. A 24 kD band seen in wild-type infections was absent.

Mutation At Leu 125

V717 contains a mutation of Leu125 to Val125. This virus did not grow on Vero cells at 31°, 34°, 37°, or 39° C., and showed no protease activity using Western blots at 20 hours after infection. A light 27 kD $N_o$ protease band was observed in the Western analysis. This band may reflect protease formed via recombination or carried over from the host range cell line PHS-23 during propagation of the virus.

Mutations At Pro 126

V718 contains a mutation of Pro126 to Gly126. This virus did not grow on Vero cells at 31°, 34°, 37°, or 39° C., but after 20 hours, substantial processing of the 80 kD protease (Pra) occurred. However, even extended incubation for 7 days failed to produce plaques. The inability of the virus to replicate may reflect a requirement for proper structural assembly of the capsid. While not wishing to be bound by theory, this may result from the protease activity not being properly synchronized with the replication cycle, i.e. the protease may be cutting itself in the cytoplasm, or that the protease activity observed in this mutant is insufficient to digest all of the assembly protein within the capsid. If so, then the intact ICP-35 protein that is retained within the capsid may block DNA packaging.

Mutations At His 148

Mutations which changed the histidine at position 148 were mixed. Changing this amino acid to Ala (V712) resulted in a small plaque phenotype and Western analysis showed a reduction in protease activity. This result was unexpected because in the prior art, the protease gene having the same mutation, but not contained within the virus showed no protease activity in in vitro assays. (Liu et al., 1992 Proc. Natl. Acad. Sci USA 89:2076–2080 and Deckman et al, J. Virology 66:7362–7367, both of which are incorporated by reference). While not wishing to be bound by theory, this surprising result may be due to a difference in the three dimensional structure of the protein within the virus environment, or the presence of a hitherto unknown accessory protein which lends activity to the protease.

Viruses V716 (His148 to Tyr148) V725 (His148 to Arg148) V729 (His148 to Lys148) were not viable on Vero cells, but each exhibited a different level of protease activity. V729 showed no protease activity by western blot analysis; V716 had greater than 50% protease activity, and V725 exhibited wild-type activity against Pra, but did not process ICP-35.

Mutations At His 61

Three mutations at Histidine 61 to Val 61 (V711), Tyr 61 (V715), and Ala 61 (V730) all created null mutant viruses and in Western analysis had the same extra bands as the V713 mutant.

Taken with the observations of the His148 mutations, the results suggest that His61 is required for protease activity, whereas His148 is not.

The following non-limiting Examples are presented to better illustrate the invention.

EXAMPLES

GENERAL METHODS

Viral Strains

Two strains of viruses were used, HSV-1 strain 17 [designated HSV-1(17)] and HSV-1 strain F [designated HSV-1 (F)]. Mutations to the protease have been made in HSV-1 (F) (see Liu et al., 1991, J. Virol. 65:5149–5156, hereby incorporated by reference) and temperature sensitive mutants have been isolated in HSV-1 (17) (see Preston, V. et al., 1983, J. Virol. 45:1056–1064, hereby incorporated by reference. Sequence analysis of the BsmI fragment revealed that the two strains differ by two amino acids (Leu300/Ser300 and Ser301/Pro301) and six silent mutations (in Pro15, Arg46, Gly84, Gln90, Gly199 and His341). To make an equivalent comparison of in vitro and in vivo studies, a protease chimera (pR731) was made. Plasmid pRHS2, containing the HSV-1 (F) protease was digested with BsmI and the 1.1 kb fragment was cloned into pR700 containing HSV-1(17) protease. Both viruses were equivalent in virus titer and plaque morphology on Vero cells.

PCR mutagenesis

Four oligonucleotides and a DNA template were amplified in two rounds of PCR to create a variety of mutated DNA fragments that were subsequently cloned into the plasmid vector pR700 and used to create the mutant viruses. The first round of PCR mutagenesis was carried out in two separate reactions. In one reaction, a positive strand oligonucleotide homologous to the DNA 5' to the first BsmI site, was paired with the negative strand oligonucleotide specified below. In the other reaction, a negative strand oligonucleotide homologous to the DNA 3' to the second BsmI site was paired with the positive strand oligonucleotide specified. The two specified oligonucleotides are complementary to each other, mutate the same amino acid residue, and most, but not all, concurrently introduce a new restriction endonuclease site. The specified DNA template (from pR700, pRHS2, or V713, below) was added to both reaction mixtures and PCR amplification initiated. In the second round of the procedure, the DNA fragments generated by the first round PCR reactions were gel purified and mixed together with oligonucleotides flanking the BsmI sites (SEQ.ID.NOS.: 4 and 5, below) and subjected to PCR amplification.

PCR mutagenesis was performed with Vent$_R$ DNA polymerase (New England Biolabs) in a DNA thermal cycler from Perkin Elmer Cetus. The cycle was melt for 1 minute at 99° C.; anneal at 40° C. for 2 minutes; extend at 71° C. for 3 minutes; for 30 cycles. The product of the second round PCR reaction and extended BsmI fragment, was digested with BsmI, gel purified, and ligated into the BsmI sites of pR700.

Oligonucleotides used for mutagenesis: Unless otherwise noted, all were obtained from Midland Certified Reagent Co., Midland, Tex. (in each pair the plus strand oligo is listed first):

5' and 3' oligonucleotides flanking the two BsmI cloning sites: 5'-GTACTCAAAAGGTCATAC-3'(SEQ.ID.NO.:4) (This oligo is 5' to the first BsmI site and was used for the generation of all mutations in the protease from amino acid 1 to 348).

5'-GGGAAACCAAACGCGGAATG-3'(SEQ.ID.NO.:5) (This oligo is 3' to the second BsmI site and was used in generation of mutations in the protease from amino acids 1 to 348.) Oligonucleotides for the temperature sensitive protease mutant (pR701):
5'-GATACGGTGCGGGCAGTACTGCCTCCGGAT-3' (SEQ.ID.NO.:6)
5'-ATCCGGAGGCAGTACTGCCCGCACCGTATC-3' (SEQ.ID.NO.:7) These oligos add a SacI site to the Ala48 to Val48 mutation.

Oligonucleotides for the temperature sensitive protease mutant (pR701):
5'-TTTTTGGCGCTCTTCGACAGCGGGGAC-3' (SEQ.ID.NO.:8)
5'-GTCCCCGCTGTCGAAGAGCGCCAAAAA-3' (SEQ.ID.NO.:9) These oligos add a SapI site at the Thr30 to Phe30 mutation.

Linker oligonucleotides (BspHI-PacI-HindIII) for pR710:
5'-CATGATTAATTA-3'(SEQ.ID.NO.:10)
5'-AGCTTAATTAAT-3'(SEQ.ID.NO.:11)

Oligonucleotides used for the His61 to Val61 mutation for pR711 construct:
5'-CCCACTCCCGATTAACGTGGACGTCCGCGCTGG-CTGCGAGGTG-3'(SEQ.ID.NO.:12)
5'-CCTCGCAGCCAGCGCGGACGTCCACGTTAATCG-GGAGTGGG-3'(SEQ.ID.NO.:13) This also adds an AatII restriction site.

Oligonucleotides used for the His148 to Ala148 mutation for pR712:
5'-CCCCGATCGCACGCTGTTCGCTGCAGTCGCGCT-GTGCGCGATCGGGCGG-3'(SEQ.ID.NO.:14)
5'-GATCGCGCACAGCGCGACTGCAGCGAACAGCG-TGCGATCGGGG-3'(SEQ.ID.NO.:15) This also adds a PstI restriction site.

Oligonucleotides used for the Ser129 to Ala129 mutation for pR713:
5'-CACCAACTACCTGCCCTCGGTCGCGCTAGCCAC-AAAACGC-CTGGGGGG-3'(SEQ.ID.NO.:16)
5'-CAGGCGTTTTGTGGCTAGCGCGACCGAGGGCA-GGTAGTTG-3'(SEQ.ID.NO.:17) This also adds a NheI restriction site.

Oligonucleotides used for the Serf29 to Ala129 mutation for pR714:
5'-CCAACTACCTGCCCTCGGTCGCCCTGGCCACAA-AACGCCTGGGG-3' (SEQ.ID.NO.:18)
5'-GCCAGGGCGACCGAGGG-3'(SEQ.ID.NO.:19)

Oligonucleotides used for the His61 to Tyr61 mutation for pR715:
5'-CCCACTCCCGATTAACGTGGACTACCGCGCTGG-CTGCGAG-GTG-3'(SEQ.ID.NO.:20)
5'-CGCGGTAGTCCACGTTA-3'(SEQ.ID.NO.:21)

Oligonucleotides used for the His 148 to Tyr148 mutation for pR716:
5'-CCCCGATCGCACGCTGTTCGCGTACGTCGCGCT-GTGCGCGA-TCGG-3'(SEQ.ID.NO.:22)
5'-GCGACGTACGCGAACAGC-3'(SEQ.ID.NO.:23)

Oligonucleotides used for the Leu125 to Val125 mutation for pR717:

5'-CACCAACTACGTGCCCTCGGTCTCCCTG-3' (SEQ.ID.NO.:24) 5'-CCGAGGGCACGTAGTTGGTGATCAGG-3' (SEQ.ID.NO.:25) This also adds a BsaAI restriction site.

Oligonucleotides used for the Pro 126 to Gly126 mutation for pR718: 5'-CAACTACCTGGGCTCGGTCTCCCTGGCC-3' (SEQ.ID.NO.:26) 5'-GAGACCGAGCCCAGGTAGTTGGTGATCAG-3' (SEQ.ID.NO.:27) This also adds a BstXI restriction site.

Oligonucleotides used for the His 148 to Arg148 mutation for pR725: 5'-CGCTGTTCGCACGCGTCGCGCTGTGCGCGATCG-3' (SEQ.ID.NO.:28) 5'-CAGCGCGACGCGTGCGAACAGCGTGCGATCG-GG-3' (SEQ.ID.NO.:29) This also adds a MulI restriction site.

Oligonucleotides used for the His 148 to Glu148 mutation for pR728: 5'-CTGTTCGCGGAAGTAGCGCTGTGCGCGATCGG-3' (SEQ.ID.NO.:30) 5'-CGCACAGCGCTACTTCCGCGAACAGCGTGCGAT-CGGG-3' (SEQ.ID.NO.:31 ) This also adds a Eco47III restriction site.

Oligonucleotides used for the His148 to Lys148 mutation for pR729: 5'-CGCTGTTCGCCAAGGTCGCGCTGTGCGCGAT-CG-3' (SEQ.ID.NO.:32) 5'-CACAGCGCGACCTTGGCGAACAGCGTGCGATC-GGG-3' (SEQ.ID.NO.:33) This also adds a StyI restriction site.

Oligonucleotides used for the His61 to Ala61 mutation for pR730: 5'-CCGATTAACGTTGACGCCCGCGCTGGCTGCGAG-GTGGG-3' (SEQ.ID.NO.:34) 5'-CAGCCAGCGCGGGCGTCAACGTTAATCGGGAG-TGGG-3' (SEQ.ID.NO.:35) This also adds a Psp1406I restriction site.

Oligonucleotides used for the Ala129 to Serf29 back mutation for pR732: 5'-CCTGCCCTCGGTAAGCTTGGCCACAAAACGCC-TGG-3' (SEQ.ID.NO.:36) 5'-GGCGTTTTGTGGCCAAGCTTACCGAGGGCAG-GTAG-3' (SEQ.ID.NO.:37) This also adds a HindIII restriction site.

Constructs: Plasmids derived from HSV-1 (F): pRHS 1: This plasmid contains HSV-1 (F) DNA base pairs 44590-54473, starting within the UL22 gene and ending within UL28. This was made by digesting HSV-1 (F) DNA with XbaI and ScaI. The 9884 base pair fragment was gel purified and subcloned into pGEM-7Zf(-) (Promega) at the XbaI and SmaI sites. pRHS2: This plasmid contains HSV-1 (F) DNA base pairs 49126-53272, staring within UL25 and ending within UL27. To prepare this plasmid, pRHS1 was digested with NotI and Nhe, and the 4148 base pair fragment was subcloned into the pGEM-7Zf(-) vector at the Bsp120I and XbaI sites. This clone was used for the creation of the host range cell line and pR711, pR712, pR713, pR714, pR715, pR716, pR725, pR728, pR729 and pR730. pR731:pRHS-2 was digested with BsmI, and the 1.1 kb fragment was then subcloned into the BsmI sites of pR700. This created a F strain protease in the 17 strain virus. pR732:V713 virus DNA was digested with NotI and the 6.5 kb fragment containing the HSV-1 protease was gel purified. This fragment was used as a template for PCR to back-mutate the Ser129 to Ala129 back to Ser. The back mutation also created a new HindIII site. The back mutation was performed to demonstrate that the mutant phenotypes observed for the various mutants of this invention were due to the mutagenesis process, and were not artifacts of the transfection procedure.

Plasmids derived from HSV-1 (17): pR700: This plasmid contains HSV-1(17) DNA base pairs 44440-57747, starting with UL22 and ending with UL28. To prepare, HSV-1 cos-28 was digested with StuI and NdeI, the 13,308 base pair fragment was gel purified and ligated into pGEM-4Z (Promega) at the NdeI and SmaI sites. This plasmid was use for both generation and sub-cloning of mutants pR701, pR717 and pR718 into the BsmI sites. pR7.10: This plasmid contains HSV-1(17) DNA base pairs 24699-49435, starting between UL10/UL11 and ending within UL25. Cos 28 was digested with PacI and BspHI and the resulting 24,736 bp fragment was subcloned with two linker oligonucleotides (SEQ.ID. NOS 10 & 11) containing BspHI-PacI-HindIII into the PacI/HindIII sites of New England Biolabs vector pNEB93. pR701: HSV-1 temperature sensitive mutant was created from pR700 by PCR mutagenesis. It has a Thr30 to Phe30 mutation which contains a SapI site and an Ala 48 to Val 48 mutation containing a new ScaI site.

Sequencing

Sequencing reactions were done using a Sequenase® Quick Denature Plasmid Sequencing kit (United States Biochemical) according to the manufacturer's instructions. S-35 dATP was obtained from Amersham.

Host Range Cell Line PHS-23 Expressing Protease.

pRHS2 was co-transfected with pSVNeo (Southern and Berg, 1982, J. Mol. Appl. Genet. 1:327–341) into Vero cells and cultured in 800 -μg/ml of G418 sulfate (GIBCO). Drug resistant cell lines were screened for the ability to complement the temperature sensitive protease virus, V701, at 39° C.

Digests

Prior to transfection, cosmid DNA and pR710 were digested with PacI. Plasmids pR700, pR701, pR711, pR712, pR713, pR714, pR715, pR7 16, pR717, pR718, pR725, pR728, pR729, pR730, and pR731 were digested with HindIII and NdeI, while pR732 was digested with XbaI. The digested DNA was precipitated in 2M final $NH_4OAc$ pH 7.5, and 2 volumes of isopropanol, centrifuged 10 minutes then washed in 70% ethanol and dried. The DNA was re-suspended in 10mM Tris, lmM EDTA pH 7.8. Restriction endonucleases were purchased from New England Biolabs and Promega (Madison, Wis.).

Western Blots

12% SDS-PAGE gels were transferred to Immobilon-P (Millipore, Bedford, Mass.) and blocked in phosphate buffered saline, 2% bovine fetal calf serum (FCS) (Hyclone Laboratories, Logan, Utah) 2% nonfat dry milk, and 0.1% Tween-20. A peptide made to correspond to the N-terminus of the protease, DAPGDRMEEPLPDRAC-NH2 (SEQ.ID.NO.:39) was conjugated to keyhole limpet hemocyanin, and was used to generate a polyclonal rabbit antibody (Multiple Peptide Systems, San Diego, Calif.). The second antibody was Goat Anti-Rabbit IgG (H+L) alkaline phosphatase conjugate (Bio-Rad, Hercules, Calif.). The Western blots were developed with an alkaline phosphatase conjugate substrate kit from Bio Rad or a with a ECL kit from Amersham.

Southern Blots

Viral DNA was digested with the restriction endonuclease corresponding to those sites which were added at the site of mutation. Agarose gels were transferred to Zeta Probe (Millipore) in 0.4M NaOH, and hybridized at room temperature with P-32 kinased oligonucleotides (below) in 5 X SSC, 20 mM Na2HPO4 pH 7.2, 7% SDS, 1 X Denhardts and 100 μg/ml herring sperm DNA for two hours, then washed in 5X SSC, 50° C. for four changes, each for 15 minutes.

Oligonucleotides used to probe Southerns: SH-2 5'-CGTATCCGGATCCAATG-3' (SEQ.ID.NO.:39) SH-10 5'-GTTAACAACATGATGCTG-3' (SEQ.ID.NO.:40)

Transfections

Vero or PHS-23 cells were plated at $3\times10^5$ cells per well in six well clusters the day before transfection. The following day the cells were washed in Delbeco's Modified Eagles Medium (DMEM) (from GIBCO, Gaithersburg, Md.) without FCS and then 1 ml of transfection cocktail was added. Transfection cocktail was made as follows. To 100 μl of DMEM media, 0.5 μg of digested DNA was added, followed by 141 μl of LiptofectAMINE™ (GIBCO). This transfection mixture was incubated for 30 minutes at room temperature, then 900 μl of DMEM was added. The cells (90% confluent) were washed twice with DMEM without FCS and then the one ml of transfection mixture was added. The transfection was incubated for 18 hours at 37° C., 5% $CO_2$. Transfected cells were then washed and fresh media, DMEM, 4% FCS, 100 units/ml penicillin and 100 μg/ml streptomycin, was added. At day six or seven the recombinant viruses were harvested and the virus was plaque purified.

Plaque Purification

After transfection, the cells were scraped off the plates and were either frozen and thawed three times, or sonicated Ser. dilutions 1:10, 1:100, 1:1000, 1:10,000, 1:100,000, and 1:1,000,000 were done in DMEM. Cells in six well clusters were incubated with 0.5 ml of each dilution, and were rocked every 15 minutes for two hours. The cells were then over-layed with 0.5% agarose, DMEM without phenol red, and 10% FCS and incubated at 37° C. in 5% $CO_2$ for three to five days. Plaques were picked with a cotton-plugged sterile Pasteur pipette by piercing the agarose and lifting a plug containing the recombinant virus. The plug was placed in a sterile eppendorf tube containing 0.5 ml of DMEM and 20% FCS. The plaque was sonicated and then repurified as described.

Recombinant virus expansion

After plaque purification the virus was expanded on Vero cells, or if the mutant was a null mutant, it was expanded on the host range cell line PHS-23 which expresses protease.

Virus titers

Expanded virus stocks were titered on Vero and PHS-23 is cells. Serial dilutions 1:10, 1:100, I:1000, 1:10,000, 1:100, 000, and 1:1,000,000 were done in DMEM. Six well clusters were then infected with 0.5 ml of each dilution, rocked every 15 minutes, and adsorbed for 2 hours at 37° C. The cells were then fed with DMEM, 4% FCS and 0.16% human IgG. (Armour, Kankakee, Ill.). Two to six days later the cells were fixed in 1 ml of methanol for 7 minutes and then air dried. Fixed cells were stained with Gemsa stain for 45 minutes, washed with water and dried. The plaques were then counted under a microscope.

Virus DNA Mini Preps

Mini preps of virus DNA were made as follows: a T-225 flask of Vero or pHS23 cells was infected at a MOI of 5 and harvested at 18 hours post infection. Cells were pelleted and then washed in PBS three times. The cells were re-suspended in 400μl 10mM Tris pH 8.0, 5mM NaCl, 5 mM EDTA and incubated on ice for 10 minutes. NP-40 was added to a final concentration of 1% and incubated for ten minutes on ice. The nuclei were pelleted at 10,000 x g for 15 minutes. The resulting supernatant solution was incubated with proteinase K (Boehringer Mannheim, Indianopolis, Ind.) 100 μg/ml at 37° C. overnight. DNA was extracted twice with phenol and once with chloroform and precipitated.

EXAMPLE 2

In order to test the mutagenesis process of this invention, the temperature sensitive mutation described by Preston et al., 1983 J. Virol. 45:1056–1064, which is hereby incorporated by reference, was made. This required the introduction of two amino acid changes. Four separate transfections were done. Vero or host range cell line PHS-23, were plated at approximately $3.0\times10^5$ cells per well in six well clusters. This resulted in a cell density of 80–90% the following day. The cells were washed in DMEM without FCS just prior to transfection. The transfection mix was then added to the cells and incubated for 18 hours at 37° C. The cells were washed 1X and 3 ml of DMEM with 4% FCS was added. At day six or seven, plaques were observed and recombinant virus was harvested. Each transfection gave rise to 50 or more plaques five to six days post transfection. Recombinant virus was titered on both Vero and PHS-23 cell lines. A minimum of four plaques were picked per transfection, all of the isolates grew and plaqued similarly. Table 2 shows the titer of both wild type HSV-1 (17) from one of the temperature sensitive (ts) mutant isolates on Vero and PHS-23 cells at 31° C. and 39° C.

TABLE 2

HSV-1 Temperature Sensitive Protease Mutants
V701 and HSV-1 titer on Host Range And Vero Cells

| HOST CELL LINE | VIRUS | TEMP °C. | TITER (pfu) |
|---|---|---|---|
| Vero | V701 | 31 | $6.2 \times 10^5$ |
| Vero | V701 | 39 | $1.2 \times 10^2$ |
| Vero | HSV-1 (17) | 31 | $1.0 \times 10^7$ |
| Vero | HSV-1 (17) | 39 | $2.1 \times 10^7$ |
| PHS-23 | V701 | 31 | $1.3 \times 10^6$ |
| PHS-23 | V701 | 39 | $1.0 \times 10^6$ |
| PHS-23 | HSV-1 (17) | 31 | $2.5 \times 10^7$ |
| PHS-23 | HSV-1 (17) | 39 | $1.0 \times 10^7$ |

What is claimed is:

1. A method of making a mutated HSV-1 virus, wherein said virus comprises a mutation selected from the group consisting of point mutations in a gene, an insertion of DNA, a deletion of DNA, and combinations thereof comprising transforming a host cell with a set of vectors comprising:

a first vector which is a plasmid that is not a cosmid comprising a section of the HSV-1 genome comprising the mutation and overlapping DNA homologous with overlapping DNA of at least one additional vector; and additional vectors, each additional vector comprising a fragment of the substantially complete HSV-1 genome and also comprising overlapping DNA which is homologous with a sequential genomic fragment contained in at least one additional vector, so that upon linearization, transfection of a host cell, replication of viral DNA and recombination of viral DNA, a mutated virus which is replicable in a wild type or host range cell line is formed.

2. A method of making an HSV-1 virus having a mutated gene comprising transforming a host cell with a set of vectors comprising:

a first vector which is a plasmid that is not a cosmid comprising a mutated gene of HSV-1 and overlapping DNA homologous with overlapping DNA of at least one additional vector; and additional vectors, each additional vector comprising a fragment of the substantially complete HSV-1 genome and also comprising overlapping DNA which is homologous with a sequential genomic fragment contained in at least one other additional vector, so that upon linearization, co-transfection of a host cell, replication of viral DNA, and recombination of viral DNA, a mutated virus which is replicable in a wild type or host range cell line is formed.

3. A method of making a mutated Herpes Simplex Type-1 Virus (HSV-1) comprising the steps of:

(a) obtaining a set of starting vectors, each starting vector comprising a fragment of the substantially complete HSV-1 genome and also comprising DNA which is overlapping DNA with a sequential genomic fragment contained in other starting vectors, so that upon linearization, co-transfection of a host cell, replication of viral DNA, and recombination of viral DNA, a virus which is replicable in a wild type or host range cell line is formed;

(b) replacing a starting vector comprising a gene which is to be mutated with: a first replacement vector which is a plasmid that is not a cosmid, the first replacement vector comprising a mutated gene and overlapping DNA; and at least one additional replacement vector comprising genomic DNA which was present in the replaced starting vector, but is not present in the first replacement vector and overlapping DNA;

(c) linearizing said vectors through restriction digestion; and (d) co-transfecting a host cell with the replacement vectors and the remaining starting vectors under conditions allowing replication of viral DNA and recombination of viral DNA to form a mutated virus which is replicable in a wild type or host range cell line.

4. A method according to claim 3 wherein the first replacement vector is made by a process comprising:

(a) creating a vector comprising a gene site which is to be mutated and overlapping DNA;

(b) defining a first restriction endonuclease site in a position 5' to the gene site which is to be mutated;

(c) defining a second restriction endonuclease site 3' of the first restriction site, to define a wild-type gene segment contained between the first and second restriction endonuclease sites;

(d) creating a mutant gene segment substantially identical to the wild-type gene segment, except for comprising a desired mutation; and (e) replacing the wild-type gene segment with the mutant gene segment by restriction digestion and ligation within the defined sites to obtain the first replacement vector.

5. A method according to claim 4 wherein the first restriction site and the second restriction site are both recognized by the same restriction enzyme.

6. A method according to claim 5 wherein the first restriction site and the second restriction site have different nucleotide sequences.

7. A method according to claim 4 wherein the second restriction site is less than about 2,000 base pairs downstream of the first restriction site.

8. A method according to claim 4 wherein the second restriction site is less than about 1,100 base pairs downstream of the first restriction site.

9. A method according to claim 8 wherein the mutant gene segment is made by PCR mutagenesis.

10. A method according to claim 9 wherein the mutant gene segment comprises a new restriction site.

11. A method of making an HSV-1 virus having a mutated protease gene comprising transforming a host cell with a set of vectors comprising:

a first vector which is a plasmid that is not a cosmid comprising amutated protease gene and overlapping DNA homologous with overlapping DNA of at least one additional vector; and additional vectors, each additional vector comprising a fragment of the complete HSV-1 genome and also comprising overlapping DNA which is homologous with a sequential genomic fragment contained in at least one other additional vector, so that upon linearization, co-transfection of a host cell, replication of vital DNA, and recombination of vital DNA, a virus having a mutated protease gene and which is replicable in a wild type or host range cell line is formed.

12. A method of making a mutated HSV-1 comprising a mutant viral protease comprising the steps of:

(a) obtaining a set of starting vectors, each starting vector comprising a fragment of the substantially complete HSV-1 genome and also comprising DNA which is overlapping DNA with a sequential genomic fragment contained in other starting vectors, so that upon linearization, co-transfection of a host cell, replication of viral DNA, and recombination, a virus which is replicable in a wild type or host range cell line is formed;

(b) replacing a starting vector comprising a protease gene which is to be mutated with a first replacement vector which is a plasmid that is not a cosmid, the first replacement vector comprising a mutated protease gene and overlapping DNA, and at least one additional replacement vector, comprising genomic DNA which was present in the replaced starting vector, but is not present in the first replacement vector along with overlapping DNA;

(c) linearizing said vectors through restriction digestion; and (d) co-transfecting a host cell with the replacement vectors and the remaining starting vectors under conditions allowing replication of viral DNA and recombination to form a mutated virus having a mutated protease gene and which is replicable in a wild type or host range cell line.

13. A method according to claim 12 wherein the first replacement vector is made by a process comprising:

(a) creating a vector comprising a protease gene site which is to be mutated and overlapping DNA;

(b) defining a first restriction endonuclease site in a position 5' to a protease gene site which is to be mutated;

(c) defining a second restriction endonuclease site downstream of the first restriction site, to define a wild-type protease gene segment contained between the first and second restriction endonuclease sites;

(d) creating a mutant protease gene segment substantially identical to the wild-type gene segment, except for comprising a desired mutation; and (e) replacing the wild-type protease gene segment by restriction digestion and ligation within the defined sites with the mutant protease gene segment to obtain the first replacement vector.

14. A method according to claim 13 wherein the first restriction site and the second restriction site are both recognized by the same restriction enzyme.

15. A method according to claim 12 wherein the restriction sites are BsmI sites.

16. A method according to claim 14 wherein the first restriction site and the second restriction site have a different nucleotide sequence.

17. A method according to claim 12 wherein the second restriction site is less than about 2,000 base pairs downstream of the first restriction site.

18. A method according to claim 17 wherein the second restriction site is less than about 1,100 base pairs downstream of the first restriction site.

19. A method according to claim 17 wherein the mutant gene segment is made by PCR mutagenesis.

20. A method according to claim 19 wherein the mutant gene segment comprises a new restriction site.

21. A method according to claim 12 wherein the first replacement vector comprises a 13.3kb HSV-1 insert.

22. A method according to claim 12 wherein the replacement vector is pR700.

23. A method according to claim 12 wherein the additional replacement vector comprises a 24.7 kb insert.

24. A method according to claim 23 wherein the additional replacement vector is pR710.

25. A set of vectors comprising:

a first vector which is a plasmid that is not a cosmid comprising a gene of HSV-1 which is mutated, and overlapping DNA homologous with overlapping DNA of at least one additional vector; and additional vectors, each additional vector comprising a fragment of the substantially, complete HSV-1 genome and also comprising overlapping DNA which is homologous with a sequential genomic fragment contained in at least one other additional vector, so that upon linearization, co-transfection of a host cell, replication of viral DNA, and recombination of viral DNA, a mutated virus which is replicable in a wild type or host range cell line is formed.

26. A host cell transformed with a set of vectors according to claim 25.

27. A metal according to claim 1 wherein the mutation is an insertion of DNA and the first vector comprises DNA to be inserted.

28. A method according to claim 1 wherein the mutation is a deletion of DNA and the first vector comprises DNA homologous to DNA flanking the DNA which is to be deleted.

* * * * *